United States Patent
Cappi et al.

(10) Patent No.: US 6,794,507 B2
(45) Date of Patent: Sep. 21, 2004

(54) COMPOUNDS THAT INHIBIT FACTOR XA ACTIVITY

(75) Inventors: Michael W. Cappi, München (DE); Thilo Fuchs, München (DE); Robert Eckl, München (DE); Silke Schabbert, München (DE)

(73) Assignee: Morphochem AG, Munich (DE)

( * ) Notice: Subject to any disclaimer, the term of this patent is extended or adjusted under 35 U.S.C. 154(b) by 0 days.

(21) Appl. No.: 10/362,149

(22) PCT Filed: Aug. 23, 2001

(86) PCT No.: PCT/EP01/09753
§ 371 (c)(1),
(2), (4) Date: Feb. 19, 2003

(87) PCT Pub. No.: WO02/16312
PCT Pub. Date: Feb. 28, 2002

(65) Prior Publication Data
US 2003/0153510 A1 Aug. 14, 2003

(30) Foreign Application Priority Data
Aug. 23, 2000 (DE) .......................... 100 41 402

(51) Int. Cl.⁷ ..................... C07D 241/04; A61K 31/495
(52) U.S. Cl. ..................... 544/386; 546/146; 546/226; 514/255; 514/307; 514/330
(58) Field of Search ................. 544/386; 514/255, 514/307, 330; 546/146, 226

(56) References Cited

FOREIGN PATENT DOCUMENTS

| DE | 196 53 036 A1 | 6/1998 |
| EP | 0 921 116 A1 | 6/1999 |
| EP | 1 020 434 A1 | 7/2000 |
| WO | WO 01 14320 A1 | 3/2001 |

*Primary Examiner*—Shailendra Kumar
(74) *Attorney, Agent, or Firm*—Edwards & Angell, LLP; Jeffrey D. Hsi; Peter F. Corless

(57) ABSTRACT

The present invention relates to compounds of formula (I):

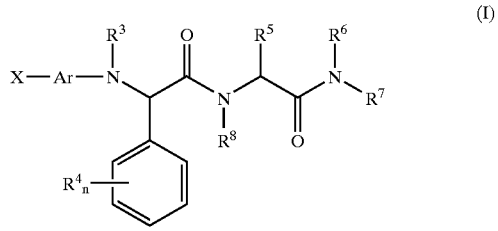

or a pharmaceutically acceptable salt, solvate, hydrate or a pharmaceutically acceptable formulation thereof. Those compounds can be used for inhibiting factor Xa and for the prevention and/or treatment of thromboembolic conditions.

19 Claims, No Drawings

COMPOUNDS THAT INHIBIT FACTOR XA ACTIVITY

This application is a 371 of PCT/EP01/09753, filed 8/23/2001

The present invention relates to novel compounds having an anticoagulating action (so-called anticoagulants) and to their pharmacologically acceptable salts and solvates and hydrates, to pharmaceutical compositions comprising them as active ingredient, to processes for the preparation of such compounds, salts and compositions, and to the use thereof for the prevention and/or treatment of thromboembolic conditions. Those compounds, salts and compositions are very effective factor Xa inhibitors. The present invention relates also to pro-drugs, optically active forms, racemates and diastereoisomers of those compounds and salts.

Thromboembolic conditions are caused by an increased tendency to blood clotting in people with risk factors, such as, for example relatively major operations, prolonged immobilisation, fractures of the lower extremities, obesity, blood fat metabolism disorders, infections with gram-negative organisms, cancer and older age.

Venous thromboses may lead to the development of oedema or inflammation of the tissue drained by the affected vein. Thrombosis of a deeper vein (so-called deep vein thrombosis) may lead to serious complications, such as, for example, pulmonary embolism. Arterial thrombosis may lead to ischaemic necrosis of the tissue supplied by the affected artery, such as, for example, to myocardial infarct in the case of an affected coronary artery. Other thromboembolic conditions are, for example, arteriosclerosis, apoplexy (stroke), Angina pectoris, Claudicatio intermittens.

Under normal physiological conditions, natural blood clotting protects against greater blood loss from a damaged blood vessel. During blood clotting, liquid blood is converted into a blood clot, a gelatinous mass which seals injured blood vessels by forming a plug. In that process, soluble fibrinogen present in the plasma is converted into the fibrous-gelatinous clotting substance fibrin in a multi-stage process, the so-called coagulation cascade.

A distinction is made between two different processes for activating blood clotting. The intrinsic blood clotting process is initiated when blood comes into contact with non-physiological surfaces. The extrinsic blood clotting process is initiated by injury to blood vessels. Both blood clotting processes join in a common process in which the blood clotting factor X, a serine protease, is converted into its active form (factor Xa). Factor Xa, together with factor Va and $Ca^{2+}$ in the so-called prothrombinase complex, causes prothrombin to be converted into thrombin which in turn, by removal of peptides, releases fibrin monomers from fibrinogen which are capable of coagulating to form fibrin fibres. Finally, factor XIII brings about cross-linking and thus stabilisation of the fibrin fibres.

Anticoagulants are used both for the prevention and for the treatment of thromboembolic conditions. As far as anticoagulants in the narrower sense are concerned, heparin, which is immediately effective and which directly inhibits certain blood clotting factors, is distinguished from the vitamin K antagonists (for example coumarin derivatives). The latter inhibit the production in the liver of certain clotting factors which is dependent on the presence of vitamin K, and begin to take effect only slowly. Other anticoagulant agents are the fibrinolytics, which bring about direct or indirect activation of the fibrinolytic system, and thrombocyte aggregation inhibitors, such as, for example, acetylsalicylic acid. A more seldom used method is reduction of the fibrinogen level in the blood by the enzyme ancrod. The object of using anticoagulant agents is to prevent the development of a blood clot that could close a vessel or also to dissolve it again once it has formed.

The above-mentioned anticoagulants in the narrower sense, i.e. heparin and vitamin K antagonists, have disadvantages. In the case of heparin, a distinction is made between unfractionated heparin (UFH) and low-molecular-weight heparin (LMWH). A disadvantage with UFH is the fact that it generally has to be administered intravenously, has a varying anticoagulant effect and therefore necessitates frequent monitoring of the patient and adaptation of the dosage. Although LMWH can be used subcutaneously in a constant, unmonitored dosage, because of its short chain length its effect is greatly reduced in comparison with UFH.

The vitamin K antagonists, such as, for example, warfarin, exhibit differing degrees of activity from patient to patient, presumably owing to genetic factors. In addition to the slow onset of action mentioned above, it involves the disadvantage that patients have to be monitored and individual adaptation of the dosage is required.

Other known anticoagulants belong to the group of the thrombin inhibitors. Current synopses of the relevant research activity in that field can be found, for example, in Jules. A. Shafer, Current Opinion in Chemical Biology, 1988, 2: 458–485, Joseph P. Vacca, Current Opinion in Chemical Biology, 2000, 4: 394–400 and in Fahad Al-Obeidi and James A. Ostrem, DDT, Vol. 3, No. 5, May 1998: 223–231.

A crucial disadvantage of thrombin inhibitors is that, in order to obtain the desired effect, it is necessary to suppress thrombin activity in vivo to such a great extent that the tendency to haemorrhage may increase, which makes dosage difficult.

In contrast, factor Xa inhibitors cause suppression of the new formation of thrombin from prothrombin, whereas they do not impair existing thrombin activity which is necessary for primary haemostasis.

In addition to the above-mentioned synoptic articles, the following may be mentioned here by way of example: DE 197 43 435, DE 197 55 268, DE 198 19 548, DE 198 39 499 and WO 0031068.

The range of action and the range of side-effects of those factor Xa inhibitors have not yet been fully investigated in some cases.

An object of the present invention was to provide novel compounds having useful properties, especially an anticoagulating action.

More precisely, the object was to provide novel factor Xa inhibitors having improved activity, reduced side-effects and/or increased selectivity. In addition, suitable pharmaceutical compositions were to be provided. Those compounds and compositions were to be administrable especially orally.

A further object of the present invention was to provide a process for the preparation of those novel compounds.

Those novel compounds were furthermore to be suitable for use in the prevention and/or treatment of thromboembolic conditions.

The present invention describes anticoagulant compounds, their pharmacologically acceptable salts and solvates and hydrates and formulations that are novel, have a high activity and selectivity and can be administered orally. The present invention further relates to pro-drugs, optically active forms, racemates and diastereoisomers of those compounds and salts. The said compounds and salts may also themselves be pro-drugs which are activated only by metabolism. Pharmaceutical compositions comprising the said compounds or salts etc. as active ingredient are also described. A number of direct and simple syntheses of the compounds, pro-drugs, salts and compositions of the invention and of intermediates that are useful in such systems is also described. The use of those active ingredients for the prevention and/or treatment of thromboembolic conditions is also described.

The present invention relates to a compound of the general formula (I):

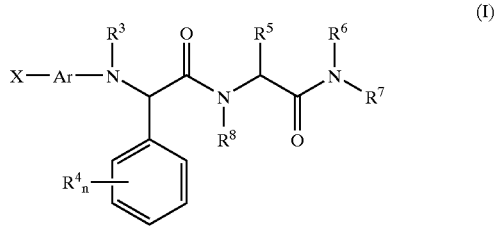

wherein

X is Cl, Br or $R^1$—N=CH(—NH$_2$)— wherein $R^1$ is H, —OH, —C(=O)OR$^2$, alkyl, aralkyl, aralkyloxy or a heteroalkyl group, such as, for example, alkoxy, acyl or acyloxy, wherein $R^2$ is alkyl, such as methyl, ethyl or tert.-butyl, heteroalkyl, a carbocyclic group, heterocycloalkyl, aryl, heteroaryl, heteroarylalkyl or aralkyl, such as benzyl;

Ar is arylene, heteroarylene, heteroarylalkylene or aralkylene, X being bonded directly to the aromatic ring system;

$R^3$ is H, alkyl, such as $C_1$–$C_4$-alkyl, heteroalkyl or aralkyl;

the groups $R^4$ independently of one another are alkyl groups that may be substituted by one or more —OH or —NH$_2$ radicals, or are heteroalkyl groups, carbocyclic groups, heterocycloalkyl groups, aryl groups, heteroaryl groups or aralkyl groups, it being possible for those groups to be substituted by one or more unsubstituted groups selected from alkyl, heteroalkyl, such as, for example, alkoxy, acyl or acyloxy, a carbocyclic group, heterocycloalkyl, aryl, heteroaryl and aralkyl, or are hydroxyl groups or glycosyloxy groups;

n is an integer from 0 to 5, preferably 0, 1 or 2 (in accordance with a preferred embodiment n=o);

$R^5$ is H, alkyl, heteroalkyl, a carbocyclic group, heterocycloalkyl, aryl, heteroaryl, heteroarylalkyl or aralkyl;

$R^6$ and $R^7$ independently of each other are H, alkyl, heteroalkyl, a carbocyclic group, heterocycloalkyl, such as, for example, aryl-heterocycloalkyl, aryl, heteroaryl, aralkyl or heteroarylalkyl, it being possible for those groups to be substituted by one or more preferably unsubstituted groups selected from alkyl, heteroalkyl, such as, for example, alkoxy, acyl or acyloxy, a carbocyclic group, heterocycloalkyl, aryl, heteroaryl, heteroarylalkyl, aralkyl, —OH and —NH$_2$, or together form part of a heterocycloalkyl ring system, especially an arylheterocycloalkyl ring system, such as, for example, aryl- or heteroaryl-piperazinyl, or of a heteroaryl ring system, it being possible for those systems to be substituted by one or more preferably unsubstituted groups selected from alkyl, heteroalkyl, such as, for example, alkoxy, acyl or acyloxy, a carbocyclic group, heterocycloalkyl, aryl, heteroaryl, heteroarylalkyl, aralkyl, —OH and —NH$_2$; and $R^8$ is H, alkyl, heteroalkyl, a carbocyclic group, heterocycloalkyl, aryl, heteroaryl, heteroarylalkyl or aralkyl or, together with $R^5$, forms part of a heterocycloalkyl ring system;

or a pharmacologically acceptable salt, solvate, hydrate or a pharmacologically acceptable formulation thereof.

Owing to their substitution, compounds of formula (I) contain one or more centres of chirality. The present invention therefore includes both all pure enantiomers and all pure diastereoisomers and also mixtures thereof in any mixing ratio.

The expression alkyl refers to a saturated or at least partially unsaturated, straight-chain or branched hydrocarbon group having, for example, from 1 to 12 carbon atoms, preferably from 1 to 6 carbon atoms, for example a methyl, ethyl, n-propyl, isopropyl, n-butyl, isobutyl, tert.-butyl, n-hexyl, 2,2-dimethylbutyl, n-octyl, allyl, isoprenyl or hexa-2-enyl group.

The expression heteroalkyl refers to an alkyl group in which one or more carbon atoms have been replaced by at least one oxygen, nitrogen, phosphorus or sulphur atom, oxygen and nitrogen being preferred, for example an alkoxy group, such as, for example, methoxy or ethoxy, or a methoxymethyl, cyano or 2,3-dioxyethyl group. The expression heteroalkyl further refers to a carboxylic acid or to a group derived from a carboxylic acid, such as, for example, acyl, acyloxy, carboxyalkyl, carboxyalkyl ester, for example methyl carboxyalkyl ester, carboxyalkylamide, alkoxycarbonyl or alkoxycarbonyloxy.

The expression carbocyclic group refers to a saturated or partially unsaturated, cyclic group that has one or more rings forming a structure that contains, for example, from 3 to 14 carbon atoms, preferably 5 or from 6 to 10 carbon atoms, for example a cyclopropyl, cyclohexyl, tetraline or cyclohex-2-enyl group. A heterocycloalkyl group may furthermore be substituted by an unsubstituted alkyl, heteroalkyl, heteroaryl or aryl group.

The expression heterocycloalkyl refers to a carbocyclic group in which one or more carbon atoms independently of one another have been replaced by an oxygen, nitrogen, phosphorus or sulphur atom. A heterocycloalkyl group may furthermore be substituted by an unsubstituted alkyl, heteroalkyl, heteroaryl or aryl group, and may, for example, be a piperidine, morpholine, N-methylpiperazine or N-phenylpiperazine group.

The expression aryl refers to an aromatic cyclic group that has one or more rings and is formed by a structure that contains, for example, from 5 to 14 carbon atoms, preferably 5 or from 6 to 10 carbon atoms. In addition, an aryl group may be substituted by unsubstituted alkyl or heteroalkyl groups, OH, CN, NO$_2$ or NH$_2$, and may, for example, be a phenyl, naphthyl, 2-, 3- or 4-methoxyphenyl, 2-, 3- or 4-ethoxyphenyl, 4-carboxyphenylalkyl or 4-hydroxyphenyl group.

The expression heteroaryl refers to an aryl group in which one or more carbon atoms independently of one another have been replaced by an oxygen, nitrogen, phosphorus or sulphur atom. Preferably, only 1 or 2 carbon atoms are replaced. Examples of such groups are the 4-pyridyl, the 2-imidazolyl, the 3-pyrazolyl and the isoquinolinyl group.

The expression aralkyl refers to groups that, in accordance with the above definitions, comprise both aryl and alkyl groups and/or carbocyclic groups, for example benzyl or tetrahydronaphthalene groups. The expression heteroarylalkyl refers to aralkyl groups in which one or more carbon atoms independently of one another have been replaced by oxygen, nitrogen, phosphorus or sulphur atoms, for example the tetrahydroisoquinolinyl group, the 2- or 3-ethyl-indolyl group or the 4-methylpyridino group.

The expressions alkyl, heteroalkyl, carbocyclic group, heterocycloalkyl, aryl, heteroaryl, heteroarylalkyl and aralkyl also refer to groups in which one or more hydrogen atoms of such groups have been replaced by fluorine, chlorine, bromine or iodine atoms or by —OH, NH$_2$ or SH radicals. Those expressions furthermore refer to corresponding groups that are substituted by unsubstituted alkyl, heteroalkyl, aralkyl or aralkyloxy groups.

The expressions arylene, heteroarylene, heteroarylalkylene and aralkylene refer to di-substituted aryl, heteroaryl, heteroarylalkyl and aralkyl groups, i.e. to groups carrying at least two substituents other than H.

In the context of the present invention, the expression "glycosyloxy group" refers to a saccharide, especially a monosaccharide, preferably glucose or fructose, that is bonded by way of an α- or β-O-glycosyl bond.

Preference is given to compounds of the general formula (I) or (II) wherein X=R$^1$—N=C(—NH$_2$)—.

Preference is also given to compounds of the general formula (I) wherein R$^1$=H, OH or C$_1$–C$_4$-alkoxy, such as methoxy or ethoxy.

Preference is given in addition to compounds of the general formula (I) wherein Ar is a substituted or unsubstituted meta-phenylene.

Special preference is given to compounds of the general formula (I) wherein Ar is a meta-phenylene substituted in the para-position to X by an OH, NH$_2$, C$_1$–C$_4$-alkoxy (for example methoxy), C$_1$–C$_4$-alkylamino or C$_2$–C$_6$-dialkylamino group or by a halogen atom (for example chlorine or fluorine).

Preference is furthermore given to compounds of the general formula (I) wherein R$^3$=H.

Preference is furthermore given to compounds of the general formula (I) wherein the groups R$^4$ independently of one another are an OH, —OCH$_2$COOH, —COOH, C$_1$–C$_4$-alkoxy or glycosyloxy group or a halogen atom, such as, for example, F or Cl. Especially preferably, R$^4$ is an —OCH$_2$COOH, —COOH or β-D-glucosyloxy group.

Preference is also given to compounds of the general formula (I) wherein R$^5$ is H, C$_1$–C$_6$-alkyl, C$_1$–C$_6$-heteroalkyl or the side chain of a natural amino acid. Especially preferably, R$^5$ is H or methyl.

Preference is also given to compounds of the general formula (I) wherein R$^6$ and R$^7$ together form part of an aryl- or heteroaryl-piperazinyl ring (especially preferably of a 4-aryl- or 4-heteroaryl-piperazinyl ring).

Preference is furthermore given to compounds of the general formula (I) wherein R$^8$=H or C$_1$–C$_6$-alkyl, such as methyl.

Preference is also given to compounds of the general formula (I) that have the following structure (II):

(II)

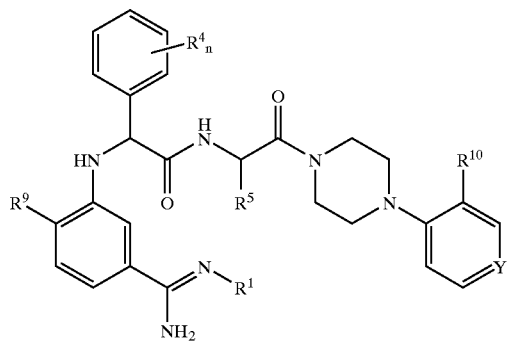

wherein R$^1$ is H, OH or C$_1$–C$_4$-alkoxy, such as methoxy or ethoxy; R$^4$ independently of one another are an OH, —OCH$_2$COOH, —COOH, C$_1$–C$_4$-alkoxy or glycosyloxy group (especially preferably a β-D-glucosyloxy group) or a halogen atom, such as, for example, F or Cl; n is 0, 1 or 2, preferably 0 or 1; R$^5$ is H or a C$_1$–C$_4$-alkyl group, such as a methyl group; R$^9$ is H, OH F or a C$_1$–C$_4$-alkoxy group (especially preferably methoxy); R$^{10}$ is H, a halogen atom (especially preferably F), CN, NO$_2$ or a C$_1$–C$_4$-alkoxy group (especially preferably methoxy); Y is N or CR$^{11}$ and R$^{11}$ is H, a halogen atom (especially preferably F), CN, NO$_2$ or a C$_1$–C$_4$-alkoxy group (especially preferably methoxy).

Examples of pharmacologically acceptable salts of compounds of formula (I) or (II) are salts of physiologically acceptable mineral acids, such as hydrochloric acid, sulphuric acid and phosphoric acid; or salts of organic acids, such as methanesulphonic acid, p-toluenesulphonic acid, lactic acid, acetic acid, trifluoroacetic acid, citric acid, succinic acid, fumaric acid, maleic acid and salicylic acid. Compounds of formula (I) or (II) can be solvated, especially hydrated. The hydration may take place, for example, during the preparation process or as a consequence of the hygroscopic nature of the initially anhydrous compounds of formula (I) or (II).

The pharmaceutical compositions according to the present invention comprise at least one compound of formula (I) or (II) as active ingredient and optionally excipients and/or adjuvants.

The pro-drugs to which the present invention also relates consist of a compound of formula (I) or (II) and at least one pharmacologically acceptable protecting group that is removed under physiological conditions, for example an alkoxy, aralkyloxy, acyl or acyloxy group, such as, for example, an ethoxy, benzyloxy, acetyl or acetyloxy group.

Compounds of formula (I) or (II) in which X is a cyano group serve as starting materials for the synthesis of said biologically active compounds. Those compounds can be synthesised by processes that are generally known for the formation of amide bonds. For example, an acid compound of formula (III) and an amine compound of formula (IV)

(III)

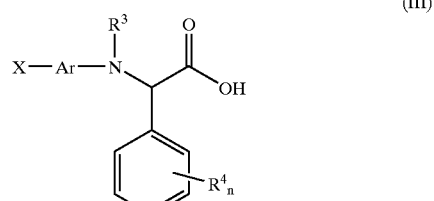

(IV)

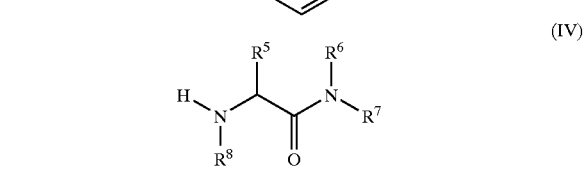

in a solvent, such as dimethylformamide, can be linked together with a coupling reagent, such as carbonyldiimidazole or dicyclohexyl carbodiimide, and 1-hydroxybenzotriazole.

Compounds of formula (III) in which X is a cyano group can be synthesised by reacting an amine of formula (V) in which X is a cyano group with an α-keto acid of formula (VI)

(V)

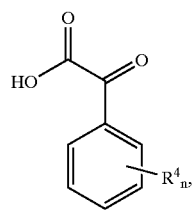
(VI)

for example in a solvent, such as ethanol or methanol, for example using sodium cyanoborohydride and catalytic amounts of acetic acid.

Alternatively, compounds of formula (III) can be synthesised by reacting an α-bromic acid with a base, such as sodium hydroxide, evaporating the solvent and adding an excess of an amine of formula (V), and heating the resulting mixture at a preferred temperature of from 80 to 120° C. over a period of several hours.

Compounds of formula (III) can alternatively be synthesised also by reacting an aldehyde, such as 3-cyanobenzaldehyde, with an amino acid in an aqueous solution of a base, such as sodium hydroxide, and adding, for example, sodium cyanoborohydride, preferably at a temperature below 5° C.

In a preferred method for the stereoselective synthesis of compounds of formula (I) or (II), compounds of formula (III) are synthesised by reacting an aryl bromide, such as, for example, 3-bromobenzonitrile, with a phenylglycine derivative, such as, for example, (S)-phenylglycine. That synthesis can be carried out, for example, analogously to the process described in: D. Ma et al., J. Amer. Chem. Soc. 1998, 120:12459–12467. In the case of the compounds prepared stereoselectively in that manner, it was found that both the compounds of formula (I) or (II) having the (R)-configuration at the phenylglycine unit and the corresponding compounds having the (S)-configuration are very effective factor Xa inhibitors, the compounds having the (S)-configuration exhibiting, with identical substitution, slightly better inhibitory properties. In the case of the second amino acid unit of the general formula (I) or (II), the compounds having the (S)-configuration are similarly the somewhat better factor Xa inhibitors, while the corresponding compounds having the (R)-configuration are also very effective factor Xa inhibitors. According to the invention, preference is therefore given to compounds of formula (I) or (II) having the S,S-configuration, with compounds having the R,S-, S,R- and R,R-configuration also exhibiting very good inhibitory properties and forming part of the invention.

Compounds of formula (IV) can be synthesised by synthesising a N-Boc-protected amino acid with an amine of formula (XI) using standard linking methods with a coupling reagent, such as carbonyldiimidazole or dicyclohexyl carbodiimide, and 1-hydroxybenzotriazole. Compounds of formula (IV) can also be synthesised by using the mixed anhydrides or 4-nitrophenyl esters of the corresponding N-Boc-protected amino acids. Removal of the protecting group at the amine group by treatment with an acid, such as hydrochloric acid, trifluoroacetic acid or formic acid, in water or dichloromethane results in the end compounds of formula (IV).

Compounds of formula (I) in which X is —CN or —C(=NH)NH$_2$ and R$^8$ is H can be synthesised according to the invention also in one step by reacting together an amine of formula (VII), an aldehyde of formula (VIII) and an isonitrile of formula (IX), for example in a solvent, such as methanol, isopropanol, ethanol, chloroform, acetonitrile, dichloromethane, or a solvent mixture, for example methanol/water, isopropanol/water, acetonitrile/water or chloroform/water.

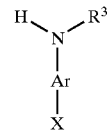
(VII)

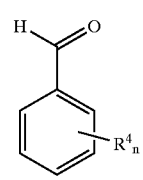
(VIII)

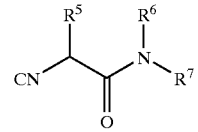
(IX)

The described reaction can be catalysed by the addition of Brönsted acids, such as p-toluenesulphonic acid or 2,4-dinitrobenzenesulphonic acid, or Lewis acids, such as zinc dichloride, iron trichloride, boron trifluoride etherate or ytterbium triflate.

Compounds of formula (IX) can be synthesised by reacting an isonitrile of formula (X) with an amine of formula (XI)

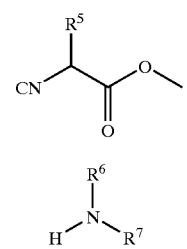
(X)

(XI)
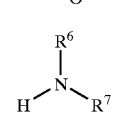

in a solvent, such as methanol, dichloromethane or dimethylformamide, or also without solvent, for example at room temperature or at a temperature up to 80° C. (cf. K. Matsumoto et al., Synthesis, 1997, 249–250).

The above-mentioned starting compounds, especially the compounds of formulae (VII), (VIII), (XI), (V) and (VI), are commercially available or can be prepared by processes known from the literature. Compounds of formula (X) can be synthesised by the known process according to I. Ugi (ed. I. Ugi, Isonitrile Chemistry in Organic Chemistry, Volume 20, Academic Press, 1971, New York and London).

To convert —CN into —C(=NH)NH$_2$, the starting nitrile can be dissolved in a solvent, such as ethanol or methanol, or a solvent mixture, such as chloroform and methanol or chloroform and ethanol, and that solution can be exposed to a stream of anhydrous hydrogen chloride at a temperature below 10° C. After a reaction time of from several hours to days, the intermediate is precipitated with ether and filtered off. That intermediate can be dissolved in water and extracted with a solvent, such as dichloromethane, chloroform or ethyl acetate, after neutralisation with a base, such as sodium carbonate or sodium hydroxide. The resulting material is then reacted with anhydrous ammonia or an ammonium salt, such as ammonium chloride, in a solvent, such as methanol or ethanol, preferably at a temperature up to 80° C. Alternatively, the filtered intermediate can be immediately reacted with anhydrous ammonia or an ammonium salt, such as ammonium chloride, in a solvent, such as methanol or ethanol.

To convert —CN into —C(=N—OH)NH$_2$, the starting nitrile can be dissolved in a solvent, such as dimethylformamide or ethanol, and the solution can be added to a reaction mixture of a base, such as sodium, sodium hydride or triethylamine, and hydroxylamine or a hydroxylamine salt, such as hydroxylamine hydrochloride, in a solvent, for example dimethylformamide or ethanol, preferably at a temperature below 5° C. To convert —CN into —C(=N—R$^1$)NH$_2$ wherein R$^1$ is alkoxy, the corresponding alkylhydroxylamine is used in place of hydroxylamine.

To convert —CN into —C(=NH)NH$_2$, conversion can first be carried out according to the above process into a compound (I) in which X is —C(=N—OH)NH$_2$. In a second step, by dissolving in a solvent, such as ethanol or acetic acid, that compound is then hydrogenated using a catalyst, for example palladium or palladium-on-carbon or platinum or Raney nickel, in a hydrogen atmosphere.

Compounds of formula (I) in which R$^1$ is —C(=O)OR$^2$ can be synthesised by reacting a compound of formula (I) in which R$^1$ is H in a solvent, such as dimethylformamide or dichloromethane, with a chloroformic acid ester of the formula ClC(=O)OR$^2$.

The compounds of formula (I) prepared by one of the processes described above can be separated into the individual stereoisomers by means of HPLC.

After synthesis, compounds of formula (I) wherein X=—C(=N—R$^1$)NH$_2$ may optionally be converted into a physiologically acceptable salt, solvate or hydrate.

A compound or pharmaceutical composition of the present invention can be used for inhibiting factor Xa activity, for the prevention and/or treatment of thromboembolic conditions, arterial restenosis, septicaemia, cancer, acute inflammation or other conditions mediated by factor X$_a$ activity, and especially venous thromboses, oedema or inflammation, deep vein thrombosis, pulmonary embolisms, thromboembolic complications after relatively major operations, in the case of vascular surgery, prolonged immobilisation, fractures of the lower extremities etc., arterial thromboses, especially of the coronary vessels in the event of myocardial infarct, and arteriosclerosis, apoplexy, Angina pectoris, Claudicatio intermittens, to mention but a few indications.

In general, as mentioned at the beginning, the active ingredients according to the invention are to have an inhibitory action towards factor Xa that is as great as possible while having a selectivity that is as high as possible. The selectivity was assessed in the present case by comparing the inhibitory action towards factor Xa and also tryptase and thrombin (two further serine proteases).

As mentioned above, the therapeutic use of the compounds of formula (I) or (II), their pharmacologically acceptable salts and solvates and hydrates and also formulations and pharmaceutical compositions are within the scope of the present invention.

The present invention relates also to the use of those active ingredients for the preparation of medicaments for the prevention and/or treatment of thromboembolic conditions. In general, compounds of formula (I) or (II) are administered either individually or in combination with any other desired therapeutic agent, using the known and acceptable modes.

Such therapeutically useful agents can be administered by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or spray, transdermally or intranasally. For the preparation of such tablets, pills, semi-solid substances, coated tablets, dragees and hard gelatin capsules, the therapeutically usable product can be mixed with pharmacologically inert, inorganic or organic excipients, for example with lactose, sucrose, glucose, gelatin, malt, silica gel, starch or derivatives thereof, talcum, stearic acid or salts thereof, skimmed milk powder and the like. For the preparation of soft capsules, excipients such as, for example, vegetable oils, petroleum, animal or synthetic oils, wax, fat and polyols can be used. For the preparation of liquid solutions and syrups, excipients such as, for example, water, alcohols, aqueous saline solution, aqueous dextrose, polyols, glycerol, vegetable oils, petroleum and animal or synthetic oils can be used. For suppositories, excipients such as, for example, vegetable oils, petroleum, animal or synthetic oils, wax, fat and polyols can be used. For aerosol formulations, compressed gases that are suitable for the purpose can be used, such as, for example, oxygen, nitrogen and carbon dioxide. The pharmaceutically acceptable agents may also contain additives for preserving and stabilising, emulsifiers, sweeteners, flavourings, salts for altering the osmotic pressure, buffers, enclosure additives and anti-oxidants.

Combinations with other therapeutic agents may comprise other active ingredients that are customarily used for the prevention and/or treatment of thromboembolic conditions, such as, for example, warfarin etc.

For the prevention and/or treatment of the conditions mentioned above, the dosage of the biologically active compound according to the invention can be varied within wide limits and can be adjusted to individual requirements. In general, a dosage of from 0.1 µg to 10 mg/kg of body weight per day is suitable, a preferred dosage being from 0.5 to 4 mg/kg per day. In suitable cases, the dosage may also be below or above the stated values.

The following Examples are intended to illustrate the invention. The stereochemistry of 3,4,5-trihydroxy-6-hydroxymethyl-tetrahydropyran-2-yloxy corresponds to that of β-D-glucose.

EXAMPLES

Example 1

A 0.05 molar solution of 2-(3,4,5-trihydroxy-6-hydroxymethyl-tetrahydropyran-2-yloxy)-benzaldehyde (helicin), a 0.05 molar solution of 3-aminobenzamidine dihydrochloride and a 0.05 molar solution of 2-isocyano-1-[4-(2-methoxy-phenyl)-piperazin-1-yl]-ethanone in methanol were reacted for 24 h at room temperature in a closed vessel. After evaporation of the solvent, the product was subjected to liquid chromatography and mass spectroscopy in order to establish the structure of the end product. The product, 2-(3-carbamimidoyl-phenylamino)-N-{2-[4-(2-methoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide, can be purified by liquid chromatography and using a water/acetonitrile gradient as eluant over a reversed phase chromatography column.

C34H42N6O9 (678.7486)

ESI-TOF-MS: 679 [M+H]+

Example 2

Analogously to Example 1 and using the corresponding suitable starting materials, 2-(3-carbamimidoyl-phenylamino)-N-{2-[4-(4-methoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C34H42N6O9 (678.7486)

ESI-TOF-MS: 679 [M+H]+

Example 3

Analogously to Example 1 and using the corresponding suitable starting materials, 2-biphenyl-4-yl-2-(3-carbamimidoyl-phenylamino)-N-{2-[4-(2-methoxy-phenyl)-piperazin-1-yl]-2-oxo-ethyl}-acetamide was obtained.

C34H36N6O3 (576.7044)

ESI-TOF-MS: 577 [M+H]+

Example 4

Analogously to Example 1 and using the corresponding suitable starting materials, 2-biphenyl-4-yl-2-(3-carbamimidoyl-phenylamino)-N-{2-[4-(4-methoxy-phenyl)-piperazin-1-yl]-2-oxo-ethyl}-acetamide was obtained.

C34H36N6O3 (576.7044)

ESI-TOF-MS: 577 [M+H]+

Example 3

Analogously to Example 1 and using the corresponding suitable starting materials, 2-(3-(carbamimidoyl-phenylamino)-2-(3,4-dimethoxy-phenyl)-N-{2-[4-(2-methoxy-phenyl)-piperazin-1-yl]-2-oxo-ethyl}-acetamide was obtained.

C30H36N6O5 (560.6586)

ESI-TOF-MS: 561 [M+H]+

Example 6

Analogously to Example 1 and using the corresponding suitable starting materials, 2-(3-(carbamimidoyl-phenylamino)-2-(3,4-dimethoxy-phenyl)-N-{2-[4-(4-methoxy-phenyl)-piperazin-1-yl]-2-oxo-ethyl}-acetamide was obtained.

C30H36N6O5 (560.6586)

ESI-TOF-MS: 561 [M+H]+

Example 7

Analogously to Example 1 and using the corresponding suitable starting materials, 2-[(3-cyano-phenylamino]-N-{2-[4-(2-methoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C34H39N5O9 (661.72)

ESI-TOF-MS: 662 [M+H]+

Example 8

0.8 mmol of the product of Example 7 was added to a methanol solution containing equimolar quantities of hydroxylamine hydrochloride and a suitable base, such as triethylamine or sodium methoxide, and stirring was carried out at room temperature for 24 h. After evaporation of all volatile components, the compound was purified by liquid chromatography analogously to Example 1. 2-[3-(N-hydroxycarbamimidoyl)-phenylamino]-N-{2-[4-(2-methoxyphenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained in the form of a slightly yellowish powder.

C34H42N6O10 (694.7480)

ESI-TOF-MS: 695 [M+H]+

Example 9

Analogously to Example 1 and using the corresponding suitable starting materials, 2-(5-carbamimidoyl-2-hydroxy-phenylamino)-N-{2-[4-(2,4-difluoro-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C33H38F2N6O9 (700.7024)

ESI-TOF-MS: 701 [M+H]+

Example 10

Analogously to Example 1 and using the corresponding suitable starting materials, [3-((3-carbamimidoyl-phenylamino)-{2-[4-(2,4-difluoro-phenyl)-piperazin-1-yl]-2-oxo-ethylcarbamoyl}-methyl)-phenoxy]-acetic acid was obtained.

C29H30F2N6O5 (580.5965)

ESI-TOF-MS: 581 [M+H]+

Example 11

Analogously to Example 1 and using the corresponding suitable starting materials, 2-(5-carbamimidoyl-2-hydroxy-phenylamino)-N-{2-[4-(2-methoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C34H42N6O10 (694.7480)

ESI-TOF-MS: 695 [M+H]+

Example 12

Analogously to Example 1 and using the corresponding suitable starting materials, 2-(3-carbamimidoyl-phenylamino)-N-{2-[4-(2-cyano-phenyl)-piperazin-1-yl]-2-oxo-ethyl}2-[2-(3,4,5-trihydroxy-6-hydroxymethyl-tetrahydro-pyran-2-yloxy)-phenyl]-acetamide was obtained.

C34H39N7O8 (673.7320)

ESI-TOF-MS: 674 [M+H]+

Example 13

Analogously to Example 1 and using the corresponding suitable starting materials, 2-(5-carbamimidoyl-pyridin-2-ylamino)-N-{2-[4-(2-methoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C33H41N7O9 (679.7362)

ESI-TOF-MS: 680 [M+H]+

Example 14

Analogously to Example 1 and using the corresponding suitable starting materials, {2-[{2-[4-(4-bromo-phenyl)-4-hydroxy-piperidin-1-yl]-2-oxo-ethylcarbamoyl}-(3-carbamimidoyl-phenylamino)-methyl]-phenoxy}-acetic acid was obtained.

C30H32BrN5O6 (638.5234)

ESI-TOF-MS: 639 [M+H]+

Example 15

Analogously to Example 1 and using the corresponding suitable starting materials, 2-(3-carbamimidoyl-phenylamino)-N-{1-[4-(2-methoxy-phenyl)-piperazine-1-carbonyl]-2-methyl-propyl}-2-phenyl-acetamide was obtained.

C31H38N6O3 (542.6869)
ESI-TOF-MS: 543 [M+H]+

Example 16

Analogously to Example 1 and using the corresponding suitable starting materials, [3-((3-carbamimidoyl-phenylamino)-{2-[4-(2-nitro-phenyl)-piperazin-1-yl]-2-oxo-ethylcarbamoyl}-methyl)-phenoxy]-acetic acid was obtained.

C29H31N7O7 (589.6131)
ESI-TOF-MS: 590 [M+H]+

Example 17

Analogously to Example 1 and using the corresponding suitable starting materials, [5-((3-carbamimidoyl-phenylamino)-{2-[4-(2,4-difluoro-phenyl)-piperazin-1-yl]-2-oxo-ethylcarbamoyl}-methyl)-2-methoxyphenoxy]-acetic acid was obtained.

C30H32F2N6O6 (610.6229)
ESI-TOF-MS: 611 [M+H]+

Example 18

Analogously to Example 1 and using the corresponding suitable starting materials, [3-((3-carbamimidoyl-phenylamino)-{2-[4-(2,4-dimethoxy-phenyl)-piperazin-1-yl]-2-oxo-ethylcarbamoyl}-methyl)-phenoxy]-acetic acid was obtained.

C31H36N6O7 (604.6686)
ESI-TOF-MS: 605 [M+H]+

Example 19

Analogously to Example 1 and using the corresponding suitable starting materials, 2-(3-carbamimidoyl-phenylamino)-N-[2-oxo-2-(4-pyridin-4-ylmethyl-piperazin-1-yl)-ethyl]-2-phenyl-acetamide was obtained.

C27H31N7O2 (485.5938)
ESI-TOF-MS: 486 [M+H]+

Example 20

Analogously to Example 1 and using the corresponding suitable starting materials, 2-(3-carbamimidoyl-phenylamino)-N-{2-[4-(2-nitro-phenyl)-piperazin-1-yl]-2-oxo-ethyl}-2-phenyl-acetamide was obtained.

C27H29N7O4 (515.5767)
ESI-TOF-MS: 516 [M+H]+

Example 21

Analogously to Example 1 and using the corresponding suitable starting materials, 2-(3-carbamimidoyl-phenylamino)-N-{2-[4-(2,4-dlifluoro-phenyl)-piperazin-1-yl]-2-oxo-ethyl}-2-phenyl-acetamide was obtained.

C27H28F2N6O2 (506.5600)
ESI-TOF-MS: 507 [M+H]+

Example 22

Analogously to Example 1 and using the corresponding suitable starting materials, 2-(3-carbamimidoyl-phenylamino)-N-{2-[4-(2,4-dlifluoro-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C33H38F2N6O8 (684.7030)
ESI-TOF-MS: 685 [M+H]+

Example 23

Analogously to Example 1 and using the corresponding suitable starting materials, 2-(3-carbamimidoyl-phenylamino)-N-[2-oxo-2-(4-pyridin-4-yl-piperazin-1-yl)-ethyl]-2-phenyl-acetamide was obtained.

C26H29N7O2 (471.5667)
ESI-TOF-MS: 472 [M+H]+

Example 24

Analogously to Example 1 and using the corresponding suitable starting materials, 2-(3-carbamimidoyl-phenylamino)-N-{2-[4-(2,4-dimethoxy-phenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C35H44N6O10 (708.7751)
ESI-TOF-MS: 709 [M+H]+

Example 25

Analogously to Example 1 and using the corresponding suitable starting materials, 2-(3-carbamimidoyl-phenylamino)-N-[2-oxo-2-(4-pyridin-4-yl-piperazin-1-yl)-ethyl]-2-[2-(3,4,5-trihydroxy-6-hydroxymethyl-tetrahydro-pyran-2-yloxy)-phenyl]-acetamide was obtained.

C32H39N7O8 (649.7097)
ESI-TOF-MS: 650 [M+H]+

Example 26

Analogously to Example 1 and using the corresponding suitable starting materials, 2-(3-carbamimidoyl-phenylamino)-N-{2-[4-(2-nitro-phenyl)-piperazin-1-yl]-2-oxo-ethyl}-2-[2, 3,4,5-trihydroxy-6-hydroxymethyl-tetrahydro-pyran-2-yloxy)-phenyl]-acetamide was obtained.

C33H39N7O10 (693.7197)
ESI-TOF-MS: 694 [M+H]+

Example 27

Analogously to Example 1 and using the corresponding suitable starting materials, 2-(3-carbamimidoyl-phenylamino)-N-{2-[4-(2,4-dimethoxy-phenyl)-piperazin-1-yl]-2-oxo-ethyl}-2-phenyl-acetamide was obtained.

C29H34N6O4 (530.6321)
ESI-TOF-MS: 531 [M+H]+

Example 28

Analogously to Example 1 and using the corresponding suitable starting materials, 2-(3-carbamimidoyl-phenylamino)-N-{2-[4-(2-methoxy-phenyl)-piperazin-1-yl]-2-oxo-ethyl}-2-phenyl-acetamide was obtained.

C28H32N6O3 (500.6056)
ESI-TOF-MS: 501 [M+H]+

Example 29

Analogously to Example 1 and using the corresponding suitable starting materials, [2-((3-carbamimidoylphenylamino)-{2-[4-(2-methoxy-phenyl)-piperazin-1-yl]-2-oxo-ethylcarbamoyl}-methyl)-phenoxy]-acetic acid was obtained.

C30H34N6O6 (574.6421)
ESI-TOF-MS: 575 [M+H]+

Example 29a

Analogously to Example 1 and using the corresponding suitable starting materials, [3-((3-carbamimidoyl-phenylamino)-{2-[4-(2-methoxy-phenyl)-piperazin-1-yl]-2-oxo-ethylcarbamoyl}-methyl)-phenoxy]-acetic acid was obtained.

C30H34N6O6 (574.6421)
ESI-TOF-MS: 575 [M+H]+

Example 30

Analogously to Example 1 and using the corresponding suitable starting materials, [2-((3-carbamimidoyl-phenylamino)-{2-[4-(2-hydroxy-phenyl)-piperazin-1-yl]-2-oxo-ethylcarbamoyl}-methyl)-phenoxy]-acetic acid was obtained.

C29H32N6O6 (560.6150)
ESI-TOF-MS: 561 [M+H]+

Example 31

Analogously to Example 1 and using the corresponding suitable starting materials, [2-((3-carbamimidoyl-phenylamino)-{2-[4-(3-cyano-phenyl)-piperazin-1-yl]-2-oxo-ethylcarbamoyl}-methyl)-phenoxy]-acetic acid was obtained.

C30H31N7O5 (569.6255)
ESI-TOF-MS: 570 [M+H]+

Example 32

Analogously to Example 1 and using the corresponding suitable starting materials, 4-((3-carbamimidoyl-phenylamino)-{2-[4-(2-methoxy-phenyl)-piperazin-1-yl]-2-oxo-ethylcarbamoyl}-methyl)-benzoic acid was obtained.

C29H32N6O5 (544.6156)
ESI-TOF-MS: 545 [M+H]+

Example 33

Analogously to Example 1 and using the corresponding suitable starting materials, 2-(3-carbamimidoyl-phenylamino)-N-[2-(4-hydroxy-4-phenyl-piperidin-1-yl)-2-oxo-ethyl]-2-phenyl-acetamide was obtained.

C28H31N5O3 (485.5910)
ESI-TOF-MS: 486 [M+H]+

Example 34

Analogously to Example 1 and using the corresponding suitable starting materials, [4-((3-carbamimidoyl-phenylamino)-{2-[4-(2-methoxy-phenyl)-piperazin-1-yl]-2-oxo-ethylcarbamoyl}-methyl)-phenoxy]-acetic acid was obtained.

C30H34N6O6 (574.6421)
ESI-TOF-MS: 575 [M+H]+

Example 35

Analogously to Example 1 and using the corresponding suitable starting materials, 2-(3-carbamimidoyl-phenylamino)-N-{2-[4-(4-methoxy-phenyl)-piperazin-1-yl]-2-oxo-ethyl}-2-phenyl-acetamide was obtained.

C28H32N6O3 (500.6056)
ESI-TOF-MS: 501 [M+H]+

Example 36

Analogously to Example 1 and using the corresponding suitable starting materials, 2-(3-carbamimidoyl-phenylamino)-2-(2-hydroxy-phenyl)-N-{2-[4-(2-methoxy-phenyl)-piperazin-1-yl]-2-oxo-ethyl}-acetamide was obtained.

C28H32N6O4 (516.6050)
ESI-TOF-MS: 517 [M+H]+

Example 37

Analogously to Example 1 and using the corresponding suitable starting materials, 2-(3-carbamimidoyl-phenylamino)-N-{[(pyridin-3-ylmethyl)-carbamoyl]-methyl}-2-[2-(3,4,5-trihydroxy-6-hydroxymethyl-tetrahydro-pyran-2-yloxy)-phenyl]-acetamide was obtained.

C29H34N6O8 (594.6297)
ESI-TOF-MS: 595 [M+H]+

Example 38

Analogously to Example 1 and using the corresponding suitable starting materials, 2-(3-carbamimidoyl-phenylamino)-N-{2-[4-(2-methoxy-phenyl)-piperazin-1-yl]-2-oxo-ethyl}-2-[3-(3-trifluoromethyl-phenoxy)-phenyl]-acetamide was obtained.

C35H35F3N6O4 (660.7022)
ESI-TOF-MS 661 [M+H]+

Example 39

Analogously to Example 1 and using the corresponding suitable starting materials, 2-(3-carbamimidoyl-phenylamino)-2-(3,4-dimethoxy-phenyl)-N-{2-[4-(4-methoxy-phenyl)-piperazin-1-yl]-2-oxo-ethyl}-acetamide was obtained.

C30H36N6O5 (560.6586)
ESI-TOF-MS: 561 [M+H]+

Example 40

Analogously to Example 1 and using the corresponding suitable starting materials, [2-benzyloxy-5-((3-carbamimidoyl-phenylamino)-{2-[4-(2-methoxy-phenyl)-piperazin-1-yl]-2-oxo-ethylcarbamoyl}methyl)-phenoxy]-acetic acid was obtained.

C37H40N6O7 (680.7674)
ESI-TOF-MS: 681 [M+H]+

Example 41

40 mmol of 3-bromobenzonitrile, 40 mmol of (S)-phenylglycine, 60 mmol of potassium carbonate and 4 mmol of copper(I) iodide were stirred in 50 ml of dry dimethylacetamide for 24 h at 100° C. under inert gas (N$_2$). After removal of the solvent, fragment I was purified by means of liquid chromatography.

20 mmol each of Boc-sarcosine, HOBt, diisopropyl carbodiimide (DIC), piperazine and triethylamine were stirred in 110 ml of dimethylformamide (DMF) at room temperature (RT) overnight. After removal of the solvent in vacuo, the resulting crude product was purified by means of column chromatography. The resulting product was stirred in a mixture of 20 ml of trifluoroacetic acid and 20 ml of dichloromethane for 5 h at room temperature. After removal of the solvent, fragment II was purified by means of liquid chromatography. 2 mmol each of fragment I, fragment II, DIC, HOBt and triethylamine were stirred in 14 ml of DMF at RT overnight. After removal of the solvent, the crude product was purified by means of liquid chromatography. To convert the cyanide into the amidine, 1 mmol of the cyanide was dissolved in 10 ml of chloroform, 5 ml of a saturated solution of hydrogen chloride in dry methanol were added thereto and the reaction mixture was left to stand for two days at 4° C. After removal of the solvent in vacuo, 20 ml of an anhydrous solution of ammonia in methanol were added thereto and stirring was carried out at RT for 4 h. The desired product, 2-(3-carbamimidoyl-phenylamino)-N-{2-[4-(2-methoxy-phenyl)-piperazin-1-yl]-2-oxo-ethyl}-N-methyl-2-phenyl-acetamide, was purified by means of HPLC.

C29H34N6O3 (514.6327)

ESI-TOF-MS: 515 [M+H]+

Example 42

Analogously to Example 1 and using the corresponding suitable starting materials, 2-(3-carbamimidoyl-phenylamino)-N-{2-[4-(2-methoxy-phenyl)-piperazin-1-yl]-1-methyl-2-oxo-ethyl}-2-phenyl-acetamide was obtained.

Analogously to Example 41, using the corresponding suitable starting materials, the four diastereoisomers were also selectively synthesised.

C29H34N6O3 (514.6327)

ESI-TOF-MS: 515 [M+H]+

Example 43

Analogously to Example 1 and using the corresponding suitable starting materials, [2-benzyloxy-5-((3-carbamimidoyl-phenylamino)-{2-[4-(2-hydroxy-phenyl)-piperazin-1-yl]-2-oxo-ethylcarbamoyl}-methyl)-phenoxy]-acetic acid was obtained.

C36H38N6O7 (666.7403)

ESI-TOF-MS: 667 [M+H]+

Example 44

Analogously to Example 1 and using the corresponding suitable starting materials, 4-((3-carbamimidoyl-phenylamino)-{2-[4-(2-nitro-phenyl)-piperazin-1-yl]-2-oxo-ethylcarbamoyl}-methyl)-benzoic acid was obtained.

C28H29N7O6 (559.5866)

ESI-TOF-MS: 560 [M+H]+

Example 45

Analogously to Example 1 and using the corresponding suitable starting materials, 2-(3-carbamimidoyl-phenylamino)-N-{[(pyridin-3-ylmethyl)-carbamoyl]-methyl}-2-quinolin-4-yl-acetamide was obtained.

C26H25N7O2 (467.5349)

ESI-TOF-MS: 468 [M+H]+

Example 46

Analogously to Example 1 and using the corresponding suitable starting materials, 2-(3-carbamimidoyl-phenylamino)-N-[2-(6,7-dimethoxy-3,4-dihydro-1H-isoquinolin-2-yl)-2-oxo-ethyl]-2-[2-(3,4,5-trihydroxy-6-hydroxymethyl-tetrahydro-pyran-2-yloxy)-phenyl]-acetamide was obtained.

C34H41N5O10 (679.7334)

ESI-TOF-MS: 680 [M+H]+

Example 47

Analogously to Example 1 and using the corresponding suitable starting materials, N-[2-(4-acetyl-4-phenyl-piperidin-1-yl)-2-oxo-ethyl]-2-(3-carbamimidoyl-phenylamino)-2-[2-(3,4,5-trihydroxy-6-hydroxymethyl-tetrahydro-pyran-2-yloxy)-phenyl]-acetamide was obtained.

C36H43N5O9 (689.7722)

ESI-TOF-MS: 690 [M+H]+

Example 48

Analogously to Example 1 and using the corresponding suitable starting materials, (3-{(3-carbamimidoyl-phenylamino)-[2-(6,7-dimethoxy-3,4-dihydro-1H-isoquinolin-2-yl)-2-oxo-ethyl-carbamoyl]-methyl}-phenoxy)-acetic acid was obtained.

C30H33N5O7 (575.6268)

ESI-TOF-MS: 576 [M+H]+

Example 49

Analogously to Example 1 and using the corresponding suitable starting materials, {3-[[2-(4-acetyl-4-phenyl-piperidin-1-yl)-2-oxo-ethylcarbamoyl]-(3-carbamimidoyl-phenylamino)-methyl]-phenoxy}-acetic acid was obtained.

C32H35N5O6 (585.6657)

ESI-TOF-MS: 586 [M+H]+

Example 50

Analogously to Example 1 and using the corresponding suitable starting materials, [3-((3-carbamimidoyl-phenylamino)-{2-[4-(2,4-difluoro-phenyl)-piperazin-1-yl]-2-oxo-ethylcarbamoyl}-methyl)-phenoxy]-acetic acid tert.-butyl ester was obtained.

C33H38F2N6O5 (636.7048)

ESI-TOF-MS: 637 [M+H]+

Example 51

Analogously to Example 1 and using the corresponding suitable starting materials, 2-(5-carbamimidoyl-2-methoxy-phenylamino)-N-{2-[4-(2-methoxyphenyl)-piperazin-1-yl]-2-oxo-ethyl}-2-[2-(3,4,5-trihydroxy-6-hydroxymethyl-tetrahydro-pyran-2-yloxy)-phenyl]-acetamide was obtained.

C35H44N6O10 (708.7751)

ESI-TOF-MS: 709 [M+H]+

Example 52

Analogously to Example 1 and using the corresponding suitable starting materials, 4-[4-((3-carbamimidoyl-phenylamino)-{2-[4-(2-methoxy-phenyl)-piperazin-1-yl]-2-oxo-ethylcarbamoyl}-methyl)-3-methoxyphenoxy]-butyric acid was obtained.

C33H40N6O7 (632.7228)

ESI-TOF-MS: 633 [M+H]+

In order to demonstrate the inhibitory action towards factor Xa activity, chromogenic peptide substrates were used. The inhibition of the amidolytic activity of factor Xa by the compounds described above was demonstrated as follows. The measurements were carried out in microtitre plates at room temperature. The compounds were dissolved in dimethyl sulphoxide and 5 µl of that solution were added to a 1 nM solution of human recombinant factor Xa (Enzyme Research Laboratories, South Bend, Ind., USA) in a buffer (pH: 8.0 and using 50 mM Tris-HCl, 100 mM NaCl, 0.1% PEG 6000 and 0.05% Tween 80). Finally, 200 µM N-methoxycarbonyl-D-norleucyl-glycyl-L-arginine-4-nitranilide acetate (Roche Diagnostics, Mannheim, Germany) in buffer were added and the hydrolysis of the substrate was monitored with a Spectra Flour Plus spectrophotometer (Tecan, Crailsheim, Germany) over a period of 20 min. The $IC_{50}$ values were calculated by means of the "GraFit 4" program produced by Erithacus Software Ltd. (Staines, Middlesex, UK). On the assumption that the kinetics comprise a competitive inhibition, it was possible to determine the $K_i$ value by the Cheng-Prusoff equation: $K_i=IC_{50}/(1+[S]/K_m])$ (Cheng and Prusoff, Biochemical Pharmacology 1973, 22: 3099–3108). The same procedure, but with tosyl-glycyl-prolyl-lysine-4-nitranilide acetate being used as the substrate in Hepes buffer (pH 7.8), was used to determine the inhibition of the proteolytic acitivity of recombinant human tryptase (Promega, Madison, Wis., USA) by the said compounds.

The $IC_{50}$ values of the above-mentioned Examples are in the range of from 1 nM to 1 µM.

What is claimed is:

1. A compound of formula (I):

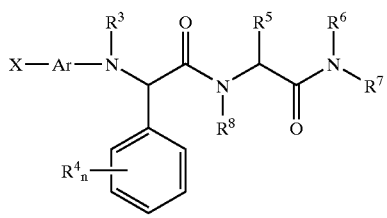

wherein

X is Cl, Br or $R^1$—N=CH(—$NH_2$)— wherein $R^1$ is H, —OH, —C(=O)$OR^2$, aralkyl, an alkyloxy or a heteroalkyl group i $R^2$ is alkyl, heteroalkyl, a carbocyclic group, heterocycloalkyl, aryl, heteroaryl, heteroarylalkyl or aralkyl;

Ar is arylene, heteroarylene, heteroarylalkylene or aralkylene, X being bonded directly to the aromatic ring system;

$R^3$ is H, alkyl, heteroalkyl or aralkyl;

the groups $R^4$ independently of one another are alkyl groups that may be substituted by one or more —OH or —$NH_2$ radicals, or are heteroalkyl groups, carbocyclic groups, heterocycloalkyl groups, aryl groups, heteroaryl groups or aralkyl groups, it being possible for those groups to be substituted by one or more unsubstituted groups selected from alkyl, heteroalkyl, a carbocyclic group, heterocycloalkyl, aryl, heteroaryl and aralkyl, or are hydroxyl groups or glycosyloxy groups;

n is an integer from 0 to 5;

$R^5$ is H, alkyl, heteroalkyl, a carbocyclic group, heterocycloalkyl, aryl, heteroaryl, heteroarylalkyl or aralkyl;

$R^6$ and $R^7$ independently of each other are H, alkyl, heteroalkyl, a carbocyclic group, heterocycloalkyl, such as, for example, aryl-heterocycloalkyl, aryl, heteroaryl, aralkyl or heteroarylalkyl, it being possible for those groups to be substituted by one or more groups selected from alkyl, heteroalkyl, a carbocyclic group, heterocycloalkyl, aryl, heteroaryl, heteroarylalkyl, aralkyl, —OH and —$NH_2$, or together form part of a heterocycloalkyl ring system, or of a heteroaryl ring system, it being possible for those systems to be substituted by one or more groups selected from alkyl, heteroalkyl, a carbocyclic group, heterocycloalkyl, aryl, heteroaryl, heteroarylalkyl, aralkyl, —OH and —$NH_2$; and $R^8$ is H, alkyl, heteroalkyl, a carbocyclic group, heterocycloalkyl, aryl, heteroaryl, heteroarylalkyl or aralkyl or, together with $R^5$, forms part of a heterocycloalkyl ring system;

or a pharmacologically acceptable salt, solvate, hydrate or a pharmacologically acceptable formulation thereof.

2. A compound according to claim 1 wherein X=$R^1$—N=C(—$NH_2$)—.

3. A compound according to claim 1 wherein $R^1$=H, OH or $C_1$–$C_4$-alkoxy.

4. A compound according to claim 1 wherein Ar is a substituted or unsubstituted meta-phenylene.

5. A compound according to claim 1 wherein Ar is substituted in the para-position to X by an OH, $NH_2$, $C_1$–$C_4$-alkoxy, $C_1$–$C_4$-alkylamino or $C_2$–$C_6$-dialkylamino group or by a halogen atom.

6. A compound according to claim 1 wherein $R^3$=H.

7. A compound according to claim 1 wherein the radicals $R^4$ independently of one another are an OH, —$OCH_2COOH$, —COOH, $C_1$–$C_4$-alkoxy or glycosyloxy group or a halogen atom.

8. A compound according to claim 1 wherein n =0, 1 or 2.

9. A compound according to claim 1 wherein $R^5$ is H, $C_1$–$C_6$-alkyl, $C_1$–$C_6$-heteroalkyl or the side chain of a natural amino acid.

10. A compound according to claim 1 wherein $R^6$ and $R^7$ together form part of an aryl-piperazinyl ring.

11. A compound according to claim 1 wherein $R^8$=H or $C_1$–$C_6$-alkyl.

12. A pharmaceutical composition comprising a compound of claim 1 and optionally excipients and/or adjuvants.

13. A method for treating a subsject suffering from a condition mediated by factor Xa activity, comprising administering to the subject an effective amount of a compound of claim 1.

14. The method of claim 13 wherein the subject is suffering from a thromoembolic condition, arterial resenosis, septicgemia, cancer or acute inflammation.

15. A method for treating a subject undergoing vascular surgery, comprising administering to the subject an effective amount of a compound of claim 1.

16. The method of claim 15 wherein the subject is susceptible to a thromboembolic condition.

17. A method of inhibiting factor Xa activity in a subject in need of such treatment, comprising administering to the subject an effective amount of a compound of claim 1.

18. A compound of claim 1 wherein $R^4$ is substituted by alkoxy, acyl or acyloxy.

19. A compound of claim 1 wherein $R^6$ or $R^7$ is alkoxy, acyl or acyloxy, or together $R^6$ and $R^7$ form an arylheterocycloc alkyl ring system.

* * * * *